United States Patent [19]

Schäfer et al.

[11] Patent Number: 5,605,898
[45] Date of Patent: Feb. 25, 1997

[54] ANELLATED TRIAZOLE COMPOUNDS

[75] Inventors: Matthias Schäfer, Goldbach; Karlheinz Drauz, Freigericht; Dieter Feit, Wächtersbach, all of Germany

[73] Assignees: Degussa AG, Frankfurt, Germany; E. I. DuPont de Nemours and Company, Wilmington, Del.

[21] Appl. No.: 424,421

[22] PCT Filed: Oct. 26, 1993

[86] PCT No.: PCT/EP93/02957

§ 371 Date: Apr. 24, 1995

§ 102(e) Date: Apr. 24, 1995

[87] PCT Pub. No.: WO94/10173

PCT Pub. Date: May 11, 1994

[30] Foreign Application Priority Data

Oct. 27, 1992 [DE] Germany .......................... 42 36 220.2

[51] Int. Cl.$^6$ .................. A61K 31/535; C07D 273/04

[52] U.S. Cl. ................ 514/229.2; 544/66; 544/68; 540/545; 548/126; 514/211; 514/364

[58] Field of Search .................. 544/66, 68; 514/229.2

[56] References Cited

FOREIGN PATENT DOCUMENTS 210137  1/1987  European Pat. Off. .

OTHER PUBLICATIONS

Hall, J. H. et al. *J. Org. Chem.* 48, 822–826 (1983).
Turner, S. R. et al. *J. Org. Chem.* 36, 2838–2840 (1971).

*Primary Examiner*—Mukund J. Shah
*Assistant Examiner*—King Lit Wong
*Attorney, Agent, or Firm*—Cushman, Darby & Cushman; Intellectual Property Group of Pillsbury Madison & Sutro

[57] ABSTRACT

Disclosed are novel anellated triazole compounds of formula, in which $R^A$, m, n, X—X, V, W and Q have the meaning stated in the specification; a method of their preapartion; and their use as herbicides.

10 Claims, No Drawings

ANELLATED TRIAZOLE COMPOUNDS

This application is the National phase of PCT/EP93/02937 filed Oct. 26, 1993. This Invention relates to novel anellated triazole compounds of the formula I

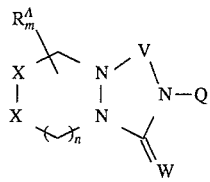

in which $R^A$, m, n, X—X, V, W and Q have the meaning stated in the specification; a method of their preparation: and their use as herbicides.

Anellated Triazole Compounds

This invention relates to novel anellated triazole compounds: a method for their preparation: and their use as herbicides.

It has already been disclosed that certain anellated triazole compounds (see EP-A 0 210 137, U.S. Pat. No. 4,560,752, GB-A 2 150 929) can be employed as herbicides.

Now novel anellated triazole compounds have been found that exhibit markedly better herbicidal activity with excellent selectivity.

The subject of the present invention therefore comprises the use of compounds of formula I as herbicides

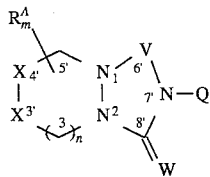

wherein X—X represents C-O, C-S or C-$NR^1$; m is 4 or 6; n is 0, 1 or 2, * means position number plus n;
W is independently of each other O or S; V is

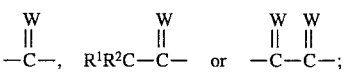

$R^A$ fill up the free 3 to 5* positions and are independently of each other, hydrogen, hydroxy (only one time each position), oxo (each reduces m by 1). haloalkyl $CO_2H$, $CO_2R^2$, halogen, CN, $C(O)NR^{11}R^{12}$ or an organic residue having up to 15 C-atoms which can be substituted, interrupted and/or combined with the heterocycle with one or more hereto atoms such as N, O or S;
Q is

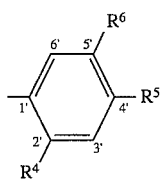

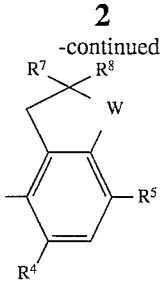

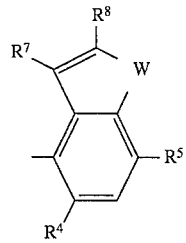

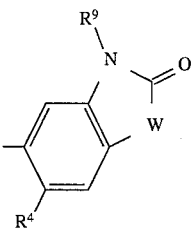

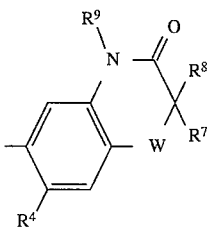

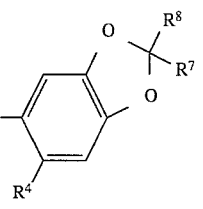

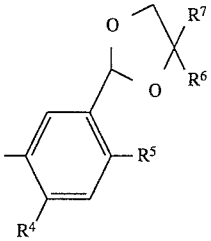

$R^1$ is hydrogen, hydroxy, halogen, $(C_1-C_8)$alkyl, CN, $(C_1-C_8)$haloalkyl, $(C_1-C_8)$alkenyl, $(C_1-C_8)$alkynyl, $COR^3$, CHO, $OR^3$, $CO_2R^2$, $C(O)SR^2$ or $C(O)NR^{11}R^{12}$;
$R^2$ is hydrogen, $(C_1-C_8)$alkyl, $(C_1-C_8)$haloalkyl, $(C_1-C_8)$alkenyl, $(C_1-C_8)$alkynyl, $COR^3$;
$R^3$ is $(C_1-C_8)$alkyl, $(C_3-C_8)$cycloalkyl, $(C_3-C_8)$alkenyl, $(C_3-C_8)$alkynyl, $(C_1C_8)$haloalkyl, $(C_2-C_8)$alkoxyalkyl, $(C_2-C_8)$carboxy alkyl, $(C_8-C_8)$alkoxycarbonylalkyl, $(C_4-C_8)$alkenyloxyalkyl, $(C_4-C_8)$alkynyloxyalkyl, $(C_3-C_8)$haloalkoxyalkyl, $(C_3-C_8)$trialkylsilyl, $(C_3-C_8)$cyanoalkyl, $(C_3-C_8)$haloalkenyl, $(C_3-C_8)$haloalkynyl, $(C_2-C_8)$alkyl carbonyl, $(C_2-C_8)$alkoxycarbonyl, $(C_2-C_8)$haloalkoxycarbonyl, $P(O)(OR^{17})_2$, $CHR^{16}P(O)(OR^{17})_2$ or $CHR^{16}P(S)OR^{16}P(S)OR^{17})_2$, phenyl or benzyl optionally substituted with halogen, $(C_1-C_3)$alkyl, $(C_1-C_3)$haloalkyl of $(C_1-C_4)$alkoxy.

Preferred are compounds of formula 1 having at least one of the following specifications
wherein $R^A$ are independently of each other, hydrogen, hydroxy, halogen, $OR^3$, $(C_1-C_8)$alkyl, $(C_1-C_8)$haloalkyl, $(C_2-C_8)$alkenl, $(C_2-C_8)$alkynyl, $S(O)_nR^3$, $COR^3$, $CO_2R^2$, $C(O)SR^2$, $C(O)NR^{11}R^{12}$ or CN:
wherein:

$R^4$ is hydrogen or halogen;

$R^5$ is $(C_1-C_2)$alkyl, $(C_1-C_2)$haloalkyl, $OCH_3$, $SCH_3$, $OCHF_2$, halogen, CN or $NO_2$:

$R^6$ is hydrogen, $(C_1-C_8)$alkyl, $(C_1-C_8)$haloalkyl, halogen, $OR^{10}$, $S(O)_nR^{10}$, $COR^{10}$, $C(O)SR^{10}$, $CO_2R^{10}$, $SCH_2C\equiv CH$, $C(O)NR^{11}R^{12}$, CHO $CH=CHCO_2R^{10}$, $CO_2N=CR^{13}R^{14}$, $NO_2$, CN, $NHSO_2R^{15}$ or $NHSO_2NHR^{15}$;

$R^7$ and $R^8$ are independently hydrogen, $(C_1-C_3)$alkyl, $(C_1-C_3)$haloalkyl or halogen; when Q is Q-2, Q-5 or Q-6, $R^7$ and $R^8$ together with the carbon to which they are attached may be C=O;

$R^9$ is hydrogen, $(C_1-C_6)$ alkyl, $(C_1-C_6)$ haloalkyl, $(C_2-C_6)$alkoxyalkyl, $(C_3-C_6)$alkenyl or $(C_3-C_6)$alkynyl;

$R^{10}$ is $(C_1-C_8)$alkyl, $(C_3-C_8)$cycloalkyl, $(C_3-C_8)$alkenyl, $(C_3-C_6)$alkynyl, $(C_1-C_8)$haloalkyl, $(C_2-C_8)$alkoxyalkyl, $(C_2-C_6)$alkylthioalkyl, $(C_2-C_8)$alkylsulfinylalkyl, $(C_2-C_8)$alkylsulfonylalkyl, $(C_3-C_8)$alkoxyalkoxyalkyl, $(C_4-C_8)$cycloalkylalkyl, $(C_2-C_4)$carboxyalkyl, $(C_3-C_8)$alkoxycarbonylalkyl. $(C_6-C_8)$alkenyloxycarbonylalkyl, $(C_6-C_8)$alkynyloxycarbonylalkyl, $(C_6-C_8)$cycloalkoxyalkyl, $(C_4-C_8)$alkenyloxyalkyl. $(C_4-C_8)$alkynyloxyalkyl, $(C_3-C_8)$haloalkoxyalkyl, $(C_4-C_8)$haloalkenyloxyalkyl, $(C_4-C_8)$haloalkynyloxyalkyl, $(C_6-C_8)$cycloalkylthioalkyl, $(C_4-C_8)$alkenylthioalkyl, $(C_4-C_8)$alkynylthioalkyl, $(C_4-C_8)$trialkylsilylalkyl, $(C_4-C_3)$cyanoalkyl, $(C_3-C_8)$halocycloalkyl, $(C_3-C_8)$haloalkenyl, $(C_5-C_8)$alkoxyalkenyl, $(C_5-C_8)$haloalkoxyalkenyl, $(C_5-C_8)$alkylthioalkenyl, $(C_5-C_8)$haloalkynyl, $(C_5-C_8)$alkoxyalkynyl, $(C_5-C_8)$haloalkoxyalkynyl, $(C_5-C_8)$alkylthioalkynyl, $(C_2-C_8)$alkylcarbonyl, $CHR^{16}COR^{17}$, $CHR^{16}P(O)(OR^{17})_2$, $P(O)(OR^{17})_2$, $CHR^{16}P(S)(OR^{17})_2$, $CHR^{16}C(O)NR^{11}R^{12}$, $CHR^{16}C(O)NH_2$, $(C_1-C_4)$alkyl substituted with phenoxy or benzyloxy optionally substituted with halogen. $(C_1-C_3)$alkyl or $(C_1-C_3)$haloalkyl; benzyl optionally substituted with halogen, $(C_1-C_3)$alkyl or $(C_1-C_3)$haloalkyl; or phenyl and pyridyl optionally substituted with halogen, $(C_1-C_3)$alkyl, $(C_1-C_3)$haloalkyl or $(C_1-C_4)$alkoxy;

$R^{11}$ and $R^{13}$ are independently hydrogen or $(C_1-C_4)$alkyl;

$R^{12}$ and $R^{14}$ are independently $(C_1-C_4)$alkyl, phenyl optionally substituted with halogen, $(C_1-C_3)$alkyl. $(C_1-C_3)$haloalkyl or $(C_1-C_4)$alkoxy;

$R^{11}$ and $R^{12}$ may be taken together as $-(CH_2)_5-$, $-(CH_2)_4-$ of $-CH_2CH_2OCH_2CH_2-$, each ring optionally substituted with $(C_1-C_3)$alkyl, phenyl of benzyl;

$R^{13}$ and $R^{14}$ may be taken together with the carbon to which they are attached to form $(C_3-C_8)$cycloalkyl;

$R^{15}$ $(C_1-C_4)$alkyl of $(C_1-C_4)$haloalkyl;

$R^{16}$ is hydrogen or $(C_1-C_3)$ alkyl;

$R^{17}$ is $(C_1-C_6)$alkyl, $(C_3-C_6)$alkenyl or $(C_3-C_6)$alkynyl.

In the above definitions, the term "alkyl", used either alone or in compound words such as "alkylthio" or "haloalkyl", includes straight chain or branched alkyl, e.g., methyl, ethyl, n-propyl, isopropyl or the different butyl isomers. Alkoxy includes e.g. methoxy, ethoxy, n-propyloxy, isopropyloxy and the different butoxy isomers. Alkenyl includes straight chain or branched alkenes, e. g., 1-propenyl, 2-propenyl, 3-propenyl and the different butenyl isomers. Cycloalkyl includes e. g. cyclopropyl, cyclobutyl, cyclopentyl and cyclohexyl. The term "halogen", either alone or in compound words such as "haloalkyl", means fluorine, chlorine, bromine or iodine. Further, when used in compound words such as "haloalkyl" said alkyl may be partially or fully substituted with halogen atoms, which may be the same or different. Examples of haloalkyl include $CH_2CH_2F$, $CF_2CF_3$ and $CH_2CHFCl$.

More preferred are compounds of formula I in which having at least the following specifications $R^A$ are, independently of each other, hydrogen, hydroxy, halogen, $OR^3$, $S(O)_nR^3$, $COR^3$, $CO_2R^2$, $(C_1-C_4)$haloalkyl, $(C_1-C_4)$alkyl, $C(O)SR^2$, $C(O)NR^{11}R^{12}$ or CN;

$R^3$ is preferred $(C_1-C_4)$alkyl, $(C_3-C_6)$cycloalkyl, $(C_3-C_6)$alkenyl, $(C_3-C_6)$alkynyl, $(C_1-C_4)$haloalkyl, $(C_2-C_4)$alkoxyalkyl, $(C_2-C_4)$carboxyalkyl, $(C_3-C_6)$alkoxycarbonylalkyl, $(C_4-C_6)$alkenyloxyalkyl, $(C_4-C_6)$alkynyloxyalkyl, $(C_3-C_6)$haloalkoxyalkyl, $(C_3-C_6)$trialkylsilyl, $(C_3-C_6)$cyanoalkyl, $(C_3-C_6)$haloalkenyl, $(C_3-C_6)$haloalkynyl, $(C_2-C_6)$alkyl carbonyl, $P(O)(OR^{17})_2$, $(C_2-C_6)$alkoxycarbonyl, $(C_2-C_6)$haloalkoxycarbonyl, $CHR^{16}P(O)(OR^{17})_2$ or $CHR^{16}P(S)(OR^{17})_2$, phenyl or benzyl optionally substituted with halogen, $(C_1-C_3)$alkyl, $(C_1-C_3)$haloalkyl or $(C_1-C_4)$alkoxy;

$R^5$ is halogen or CN;

$R^6$ is hydrogen, $(C_1-C_4)$alkyl, $(C_1-C_4)$haloalkyl, halogen, $OR^{10}$, $S(O)_nR^{10}$, $COR^{10}$, $CO_2R^{10}$, $C(O)SR^{10}$, $SCH_2C\equiv CH$, $C(O)NR^{11}R^{12}$, $CH=CHCO_2R^{10}$, $CO_2N=CR^{13}R^{14}$, $NHSO_2R^{15}$ or $NHSO_2NHR_{15}$;

$R^7$ and $R^8$ are independently hydrogen, $(C_1-C_3)$alkyl or $(C_1-C_3)$haloalkyl; when Q is Q-2 or Q-6, $R^7$ and $R^8$ together with the carbon to which they are attached may be C=O;

$R^9$ is hydrogen, $(C_1-C_4)$alkyl, $(C_1-C_4)$haloalkyl, $(C_2-C_4)$alkoxyalkyl, $(C_3-C_6)$alkenyl or $(C_3-C_6)$alkynyl;

$R^{10}$ is $(C_1-C_4)$alkyl, $(C 3-C_6)$cycloalkyl, $(C_3-C_6)$alkenyl, $(C_3-C_6)$alkynyl, $(C_1-C_4)$haloalkyl, $(C_2-C_4)$alkoxyalkyl, $(C_2-C_4)$alkylthioalkyl, $(C_2-C_4)$alkylsulfinylalkyl, $(C_2-C_4)$alkylsulfonylalkyl, $(C_3-C_6)$alkoxyalkoxyalkyl, $(C_4-C_8)$cycloalkylalkyl, $(C_2-C_4)$carboxyalkyl, $(C_3-C_6)$alkoxycarbonylalkyl, $(C_6-C_8)$alkenyloxycarbonylalkyl, $(C_6-C_8)$alkynyloxycarbonylalkyl. $(C_6-C_8)$cycloalkoxyalkyl, $(C_4-C_6)$alkenyloxyalkyl, $(C_4-C_6)$alkynyloxyalkyl, $(C_3-C_6)$haloalkoxyalkyl, $(C_4-C_8)$haloalkenyloxyalkyl. $(C_4-C_6)$haloalkynyloxyalkyl, $(C_6-C_8)$cycloalkylthioalkyl, $(C_4-C_6)$alkenylthioalkyl, $(C_4-C_6)$alkynylthioalkyl, $(C_4-C_8)$trialkylsilylalkyl, $(C_3-C_4)$cyanoalkyl, $(C_3-C_6)$halocycloalkyl, $(C_3-C_6)$haloalkenyl, $(C_5-C_6)$alkoxyalkenyl, $(C_3-C_6)$haloalkoxyalkenyl, $(C_5-C_6)$alkylthioalkenyl, $(C_3-C_6)$haloalkynyl, $(C_5-C_6)$alkoxyalkynyl, $(C_5-C_6)$haloalkoxyalkynyl, $(C_5-C_6)$alkylthioalkynyl, $(C_2-C_4)$alkyl carbonyl, $CHR^{16}COR^{17}$, $CHR^{16}P(O)(OR^{17})_2$, $P(O)(OR^{17})_2$, $CHR^{16}P(S)(OR^{17})_2$, $CHR^{16}C(O)NR^{11}R^{12}$, $CHR^{16}C(O)NH_2$, $(C_1-C_2)$alkyl substituted with phenoxy of benzyloxy optionally substituted with halogen, $(C_1-C_3)$alkyl of $(C_1-C_3)$haloalkyl; benzyl optionally substituted with halogen, $(C_1-C_2)$alkyl of $(C_1-C_2)$haloalkyl; or phenyl and pyridyl optionally substituted with halogen, $(C_1-C_3)$alkyl, $(C_1-C_3)$haloalkyl or $(C_1-C_4)$alkoxy;

$R^{12}$ and $R^{14}$ are independently $(C_1-C_2)$alkyl, phenyl optionally substituted with halogen, $(C_1-C_2)$alkyl, $(C_1-C_2)$haloalkyl or $(C_1-C_2)$alkoxy;

$R^{11}$ and $R^{12}$ may be taken together as $-(CH_2)_5-$, $-(CH_2)_4-$ or $-CH_2CH_2OCH_2CH_2-$. each ring optionally substituted with $(C_1-C_2)$alkyl, phenyl or benzyl;

$R^{13}$ and $R^{14}$ may be taken together with the carbon to which they are attached to form $(C_3-C_6)$cycloalkyl;

$R^{17}$ is $(C_1-C_4)$alkyl, $(C_3-C_6)$alkenyl or $(C_3-C_6)$alkynyl.

The position of the heteroatoms concerning X—X respectively the carbonyl functionality of V in the molecule is optionally.

Particularly preferred are compounds of formula II in which V is

Most preferred are compounds of formula II with at least one of the following specifications V is and in Q $R^4$ is fluoro or chloro;

$R^5$ is chloro;

$R^6$ is $OR^{10}$, $CO_2R^{10}$, $NHSO_2R^{10}$ or $SR^{10}$;

$R^7$ is hydrogen;

$R^8$ is hydrogen or methyl;

$R^9$ is hydrogen, $(C_3-C_4)$ alkenyl or $(C_3-C_4)$ alkynyl;

$R^{10}$ is $(C_1-C_4)$alkyl, $(C_3-C_6)$cycloalkyl, $(C_3-C_6)$alkenyl, $(C_3-C_4)$alkynyl, $(C_1-C_3)$haloalkyl, $(C_2-C_4)$alkoxyalkyl, $(C_3-C_6$-alkoxycarbonylalkyl, $(C_6-C_8)$alkenyloxycarbonylalkyl, $(C_6-C_8)$alkynyloxycarbonylalkyl or $(C_1-C_2)$carboxyalkyl.

If not otherwise specified the invention relates to both the individual possible stereoisomers of formula I and also mixtures of the isomers.

DETAILS OF THE INVENTION

The novel anellated triazole compounds of general formula I are obtained in accordance with the invention by a general method A if dioxazine derivatives of general formula III in which X—X, n, $R^A$, W, m and O have the meanings indicated above, are reacted with phosgene or a phosgene substitute such as diphosgene ($ClC(=O)OCCl_3$) or with a species introducing a $C_2$-unit, whereas, such species are defined as V like $-C=O$, $R^1R^2C-C=O$ and $-C(=O)C(=O)$. Preferred compounds of type V are oxalylic chloride and derivatives thereof or α-bromo acetic acid and derivatives. Optionally these reactions are done in an inert organic solvent, for example in an aromatic solvent such as toluene, chlorobenzene, a halogenated hydrocarbon such as chloroform, methylene chloride, an ether such as diisopropyl ether, or in acetonitrile or dimethylformamide, optionally with base catalysis preferred at temperatures of 20° to 120° C. Preferably used as bases are organic bases, for example organic amines such as triethylamine or also pyridine. The bases are used as acid acceptor optionally in the presence of activated charcoal.

Compounds of general formula III can be obtained, compounds of general formula IV in which W has the meanings indicated above, are reacted with ketons or aldehyds of general formula V.

in which $R^1$ and $R^2$ have the meanings indicated above optionally in an inert solvent, for example in an aromatic solvent such as toluene, chlorobenzene, a halogenated hydrocarbon such as chloroform, methylene chloride, an ether such as diisopropyl ether, or in acetonitril or dimethylformamide, optionally with an acid catalysis preferred at temperatures of 20° to 120° C. Preferably used acids are organic acids, example organic sulfonic acids as paratoluene sulfonic acid.

Compounds of general formula IV are obtained by reacting hydrazino ethanol of formula VI with arylisocyanates or arylisothiocyanates of general formula VII optionally in an inert organic solvent, for example in an aromatic solvent such as toluene, chlorobenzene, a halogenated hydrocarbon such as chloroform, methylene chloride, an ether such as diisopropyl ether, or in acetonitrile or dimethylformamide, optionally with base catalysis preferred at temperatures of 20° to 120° C. Preferably used as bases are organic bases, for example organic amines such as triethylamine or also pyridine.

A further subject of the invention is a method 8 for the preparation of compounds of formula I by reacting compounds of general formula VIII

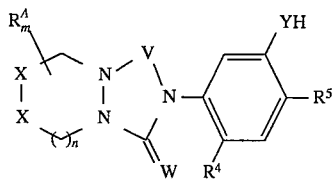
VIII wherein X—X, m, n, V, $R^A$, $R^4$ and $R^5$ have the meaning indicated above and Y=O, S, NH with a halide of the formula IX, X or XI, $$R^{10}-Z \qquad \text{IX}$$
$$R^{15}SO_2-Z \qquad \text{X}$$
$$R^{15}NHSO_2-Z \qquad \text{XI}$$

wherein Z is a chlorine-, bromine—or an iodine atom and $R^{10}$ and $R^{15}$ have the meaning indicated above.

The compounds of formula VII are known or can be prepared by analogy with known methods: see Houben-Weyl, "Methoden der organischen Chemie" [Methods of Organic Chemistry], Vol. VIII, p. 120 (1952), Houben-Weyl, Vol. IX, pp. 875, 869 (1955); EP-B 0 070 389; U.S. Pat. No. 4,881,967; EP-A 0 322 401; U.S. Pat. No. 3,495,967 EP-A 0 300 307 EP-A 0 349 832.

It may be that some of the compounds of formula I are difficult to synthesize or of little stability. Such compounds are normally not preferred. Preferred are compounds which are with respect to their desired application easy to prepare and stable enough for use. For biodegradation instability can be an advantage for the purpose of use.

Finally, it was found that the novel anellated triazole compounds of general formula I and II exhibit outstanding herbicidal qualities.

CHEMICAL EXAMPLES

Intermediate 1

N-amino-N-(2-hydroxyethyl)-N'-(4'-chlorophenyl)urea 7.61 g (0.10 mol) Hydrazino ethanol was dissolved in. 100 mol of methylene chloride at 0°–5° C. After 10.2 g (0.10 mol) triethylamine was added dropwise, 15.3 g (0.10 mol) 4-chlorophenylisocyanat was added solved in 70 ml methylene chloride over a period of four hours. The reaction mixture was allowed to warm up to room temperature, the precipitate was filtered, washed with methylene chloride and dried to give 14.3 g (62%) of the desired compound (m. p. 141°–142° C.).

EXAMPLE 2

Tetrahydro-N-(4'-chlorophenyl)-4H-1,3,4-oxadiazine-4-carboxamide

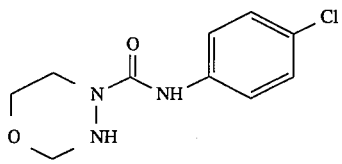

14.2 g (0.62 mol) of N-amino-N-(2-hydroxyethyl)-N'-(4'-chlorphenyl)urea (intermediate 1) was suspended in 400 ml of methylene chloride. 5.20 g (37%, 4.4 mmol) oxymethane and a small amount of para-toluene-sulfonic acid was added, before the reaction mixture was heated in a Dean-Stark apparatus for 17 h. The solvent was removed and 12.4 g (83%) of the desired compound could be isolated as a white solid with a m. p. of 110°–112° C.

EXAMPLE 3

8-(4'-Chlorophenyl)-4-oxa-7,9-dioxo-1,2,8-triaza[4.3.0] nonane:

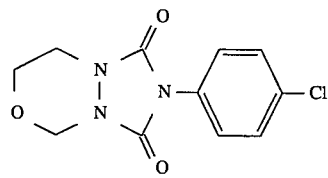

1.50 g (6.20 mmol) Tetrahydro-N-(4'-chlorophenyl)-4H-1,3,4-oxadiazine-4-carboxamide was dissolved in 30 ml toluene 1 ml triethylamine and a small amount of activated charcoal at 0°–5° C. 1.35 g (6.81 mmol). diphosgene solved in 30 ml toluene was added dropwise in 1.5 h. The reaction mixture was allowed to warm up to room temperature and was stirred overnight. The charcoal was removed by filtration and the solvent was evaporated. After silica gel column chromatography 1.50 g (90%) 8-(4'-Chlorophenyl)-4-oxa-7, 9-dioxo-1,2,8-triaza[4.3.0]nonane could be isolated as a colourless solid with a m. p. of 177°–179° C.

EXAMPLE 4

8-(4'-Chloro-2'-fluoro-5'-carboisopropoxyphenyl)-4-oxa-7,9-dioxo-1,2,8-triaza[4.3.0]nonane:

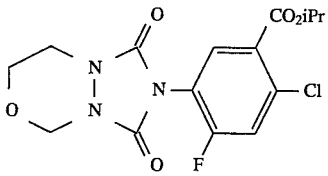

1.50 g (4.34 mmol) Tetrahydro-N-(4'-chloro-2'-fluoro-5'-carboisopropoxyphenyl)-4H-1,3,4-oxadiazine-4-carboxamide was dissolved in 30 ml toluene and 1.25 mol triethylamine and a small amount of activated charcoal was added at 0°–5° C. 0.90 g (4.40 mmol) diphosgene solved in 30 ml of toluene was added dropwise in 30 minutes. The reaction mixture was allowed to warm up to room temperature overnight, before warmed up to 55° C. for 2 h. The charcoal was removed by filtration and the solvent of the filtrate was evaporated. Silica gel, column chromatography delivers 0.105 g (63%) of 8-(4'-Chloro-2'-fluoro-5'-carboisopropoxyphenyl)-4-oxa-7,9-dioxo-1,2,8-triaza-[4.3.0]nonane as a colourness solid with a m. p. of 136°–139° C.

EXAMPLE 5

6-(4-Chloro-phenyl)-dihydro-2-oxa-4a,6,8a-triaza-naphthalene-5,7,8-trione

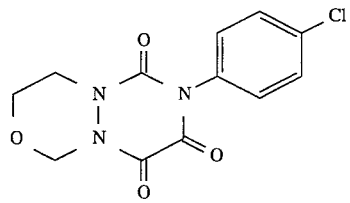

1.50 g (6.20 mmol) Tetrahydro-N-(4'-chlorophenyl)-4H-1,3,4-oxadiazine-4-carboxamide was dissolved in 30 ml of tetrahydrofuran. After addition of 0.63 g (6.20 mmol) of triethylamine, 0.76 g (6.20 mmol) oxalylic acid mono methyl ester chloride was added and refluxed. After 12 h of reflux the reaction mixture was allowed to cool to roomtemperature and the solvent evaporated. 30 ml of acetic acid methyl ester was added and the reaction mixture twice washed with 10 ml of water, before dried of $MgSO_4$. Removal of the solvent was followed by purification through column chromatography ($SiO_2$) to isolate: 1.05 g (63%) of the desired compound.

Analogously to the Examples described and in accordance with the general description of the methods A and B in accordance with the invention, the compounds of general formula I listed in the following tables can be prepared:

TABLE 1

| $R^4$ | $R^5$ | $R^6$ | melting point °C. |
|---|---|---|---|
| H | Cl | H | 177–179 |
| H | Br | H | |
| H | $CH_3$ | H | |
| F | Cl | H | |
| Cl | Cl | H | |
| F | Cl | $OCH(CH_3)_2$ | 99–102 |
| F | Cl | $OCH_2C\equiv CH$ | 191–194 |
| F | Cl | $OCH(CH_3)C\equiv CH$ | |
| F | Cl | $OCH_3$ | |
| F | Cl | $OCH_2CH_2CH_3$ | |
| F | Cl | $OCH_2CH=CH_2$ | 144–147 |
| F | Cl | $OCH_2CO_2CH_3$ | |
| F | Cl | $OCH_2CO_2CH_2C\equiv CH$ | |
| F | Cl | $OCH_2CO_2C_5H_{11}$ | |
| F | Cl | CN | |
| F | Cl | $SCH_3$ | |
| F | Cl | $OCH_2C_6H_5$ | 160–163 |
| F | Cl | $SCH(CH_3)_2$ | |
| F | Cl | $SCH_2CH=CH_2$ | |
| F | Cl | $SCH_2C\equiv CH$ | |
| F | Cl | $SCH_2CO_2H$ | |
| F | Cl | $SCH_2CO_2CH_3$ | |
| F | Cl | $OCH_2CON(CH_3)(OCH_3)$ | |
| F | Cl | $OC(CH_3)=N-OCH_3$ | |
| F | Cl | $SCH_2CO_2CH_2C\equiv CH$ | |
| F | Cl | $OCHF_2$ | |
| F | Cl | $OCH_2C(Cl)=CH_2$ | |
| F | Cl | $OCF_2CHFCl$ | |
| F | Cl | $NHSO_2CH_3$ | |
| F | Cl | $NHSO_2CH(CH_3)_2$ | |
| F | Cl | $NHSO_2NHCH_3$ | |
| F | Cl | $NHSO_2NHCH_2CH_3$ | |
| F | Cl | $CO_2CH(CH_3)_2$ | 136–139 |
| F | Cl | $CO_2CH_2CH_2CH_3$ | |
| F | Cl | $CO_2CH_2CF_3$ | |
| F | Cl | $CON(CH_3)_2$ | |
| F | Cl | $CO_2CH(CH_3)CH_2CH_3$ | |
| F | Cl | $CO_2CH(CH_3)CF_3$ | |
| F | Cl | CO—N(morpholine) | |
| F | Cl | $CO_2CH(CH_3)CH_2SCH_3$ | |
| Cl | Cl | H | |
| Cl | Cl | $OCHF_2$ | |
| Cl | Cl | $OCH(CH_3)_2$ | |
| Cl | Cl | $OCF_2CHFCl$ | |
| Cl | Cl | $OCH_2C\equiv CH$ | |
| F | Cl | $OCH_2P(O)(OC_2H_5)_2$ | |
| Cl | Cl | $OCH(CH_3)C\equiv CH$ | |
| F | Cl | $OCH_2C(O)N(CH_3)_2$ | |
| F | Cl | $O(CH_2)_2OCH_2CH_3$ | |
| Cl | Cl | $SCH_2C\equiv CH$ | |
| Cl | Cl | $SCH_2CO_2H$ | |
| Cl | Cl | $SCH_2CO_2CH_2C\equiv CH$ | |
| Cl | Cl | $NHSO_2CH_3$ | |
| F | Cl | $NHSO_2CF_3$ | |
| Cl | Cl | $CO_2CH(CH_3)_2$ | |
| Cl | Cl | $CO_2CH(CH_3)CH_2SCH_3$ | |
| Cl | Cl | $CO_2CH(CH_3)CF_3$ | |
| Cl | Cl | $CON(CH_3)_2$ | |
| F | Cl | $CO_2CH_2C\equiv CH$ | |
| F | Cl | $CO_2CH(CH_3)C\equiv CH$ | |
| Cl | Cl | $CO_2CH_2CF_3$ | |
| F | Cl | $CO_2CH(CH_3)_2$ | |
| F | Cl | $CO_2CH_3$ | |
| F | Cl | $CO_2CH_2CH_3$ | |
| F | Cl | $CO_2(CH_2)_2CH_3$ | |
| F | Cl | $OCHF_2$ | |
| F | Cl | $SCH_2CO_2H$ | |
| F | Cl | $SCH_2CO_2CH_3$ | |
| F | Cl | $NHSO_2CH_2CH_3$ | |
| F | Cl | $NHSO_2CH(CH_3)_2$ | |

TABLE 1-continued

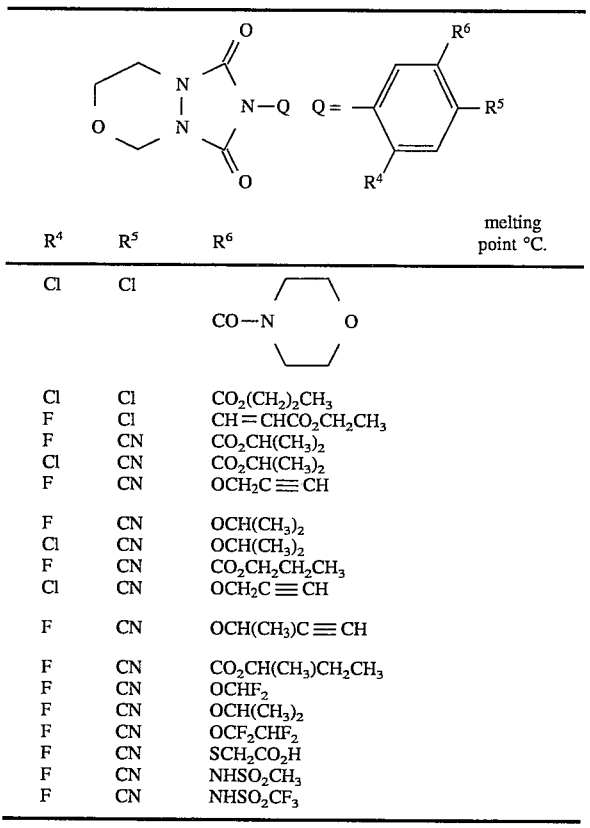

| $R^4$ | $R^5$ | $R^6$ | melting point °C. |
|---|---|---|---|
| Cl | Cl | CO—N(morpholine) | |
| Cl | Cl | $CO_2(CH_2)_2CH_3$ | |
| F | Cl | $CH=CHCO_2CH_2CH_3$ | |
| F | CN | $CO_2CH(CH_3)_2$ | |
| Cl | CN | $CO_2CH(CH_3)_2$ | |
| F | CN | $OCH_2C\equiv CH$ | |
| F | CN | $OCH(CH_3)_2$ | |
| Cl | CN | $OCH(CH_3)_2$ | |
| F | CN | $CO_2CH_2CH_2CH_3$ | |
| Cl | CN | $OCH_2C\equiv CH$ | |
| F | CN | $OCH(CH_3)C\equiv CH$ | |
| F | CN | $CO_2CH(CH_3)CH_2CH_3$ | |
| F | CN | $OCHF_2$ | |
| F | CN | $OCH(CH_3)_2$ | |
| F | CN | $OCF_2CHF_2$ | |
| F | CN | $SCH_2CO_2H$ | |
| F | CN | $NHSO_2CH_3$ | |
| F | CN | $NHSO_2CF_3$ | |

TABLE 2

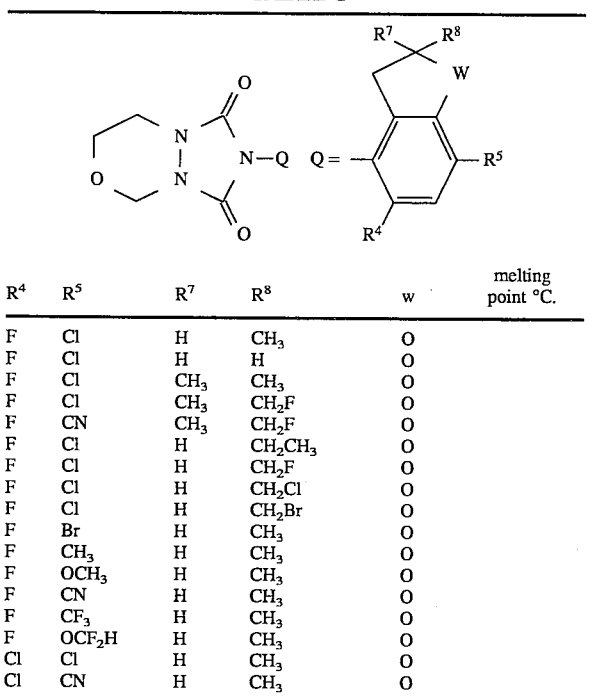

| $R^4$ | $R^5$ | $R^7$ | $R^8$ | w | melting point °C. |
|---|---|---|---|---|---|
| F | Cl | H | $CH_3$ | O | |
| F | Cl | H | H | O | |
| F | Cl | $CH_3$ | $CH_3$ | O | |
| F | Cl | $CH_3$ | $CH_2F$ | O | |
| F | CN | $CH_3$ | $CH_2F$ | O | |
| F | Cl | H | $CH_2CH_3$ | O | |
| F | Cl | H | $CH_2F$ | O | |
| F | Cl | H | $CH_2Cl$ | O | |
| F | Cl | H | $CH_2Br$ | O | |
| F | Br | H | $CH_3$ | O | |
| F | $CH_3$ | H | $CH_3$ | O | |
| F | $OCH_3$ | H | $CH_3$ | O | |
| F | CN | H | $CH_3$ | O | |
| F | $CF_3$ | H | $CH_3$ | O | |
| F | $OCF_2H$ | H | $CH_3$ | O | |
| Cl | Cl | H | $CH_3$ | O | |
| Cl | CN | H | $CH_3$ | O | |

TABLE 2-continued

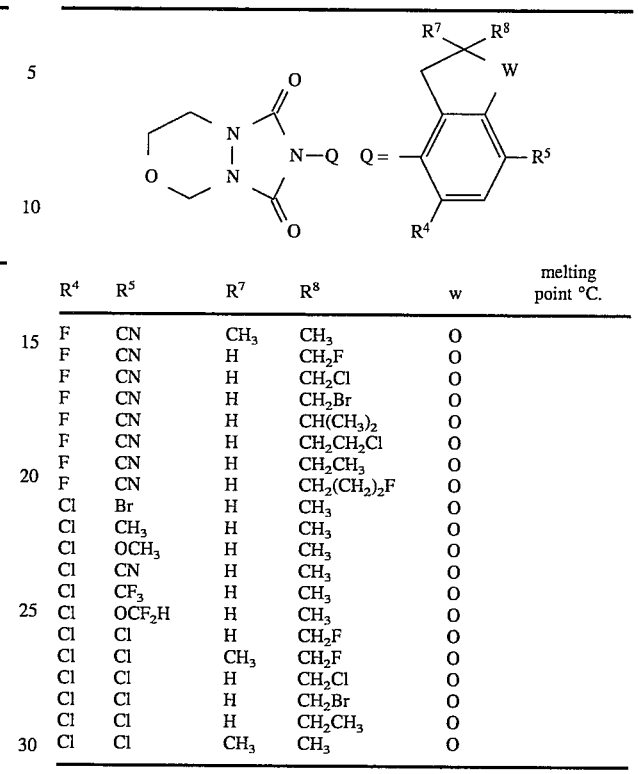

| $R^4$ | $R^5$ | $R^7$ | $R^8$ | w | melting point °C. |
|---|---|---|---|---|---|
| F | CN | $CH_3$ | $CH_3$ | O | |
| F | CN | H | $CH_2F$ | O | |
| F | CN | H | $CH_2Cl$ | O | |
| F | CN | H | $CH_2Br$ | O | |
| F | CN | H | $CH(CH_3)_2$ | O | |
| F | CN | H | $CH_2CH_2Cl$ | O | |
| F | CN | H | $CH_2CH_3$ | O | |
| F | CN | H | $CH_2(CH_2)_2F$ | O | |
| Cl | Br | H | $CH_3$ | O | |
| Cl | $CH_3$ | H | $CH_3$ | O | |
| Cl | $OCH_3$ | H | $CH_3$ | O | |
| Cl | CN | H | $CH_3$ | O | |
| Cl | $CF_3$ | H | $CH_3$ | O | |
| Cl | $OCF_2H$ | H | $CH_3$ | O | |
| Cl | Cl | H | $CH_2F$ | O | |
| Cl | Cl | $CH_3$ | $CH_2F$ | O | |
| Cl | Cl | H | $CH_2Cl$ | O | |
| Cl | Cl | H | $CH_2Br$ | O | |
| Cl | Cl | H | $CH_2CH_3$ | O | |
| Cl | Cl | $CH_3$ | $CH_3$ | O | |

TABLE 3

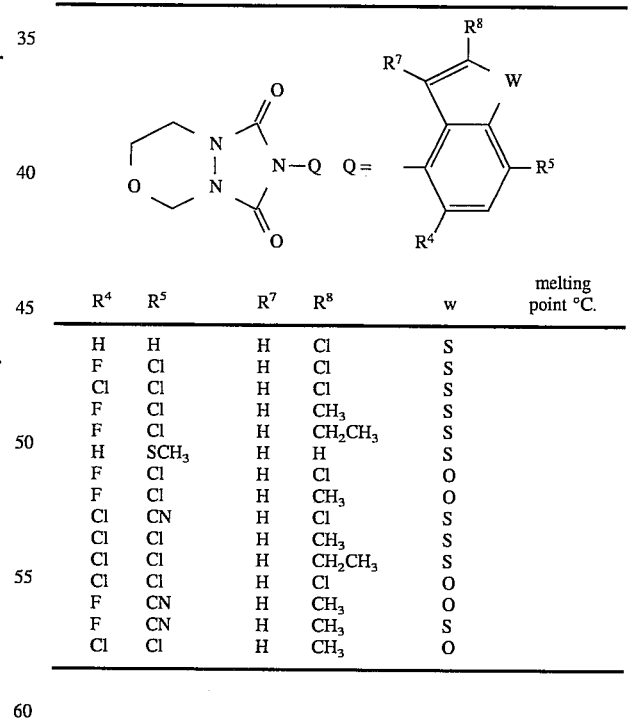

| $R^4$ | $R^5$ | $R^7$ | $R^8$ | w | melting point °C. |
|---|---|---|---|---|---|
| H | H | H | Cl | S | |
| F | Cl | H | Cl | S | |
| Cl | Cl | H | Cl | S | |
| F | Cl | H | $CH_3$ | S | |
| F | Cl | H | $CH_2CH_3$ | S | |
| H | $SCH_3$ | H | H | S | |
| F | Cl | H | Cl | O | |
| F | Cl | H | $CH_3$ | O | |
| Cl | CN | H | Cl | S | |
| Cl | Cl | H | $CH_3$ | S | |
| Cl | Cl | H | $CH_2CH_3$ | S | |
| Cl | Cl | H | Cl | O | |
| F | CN | H | $CH_3$ | O | |
| F | CN | H | $CH_3$ | S | |
| Cl | Cl | H | $CH_3$ | O | |

TABLE 4

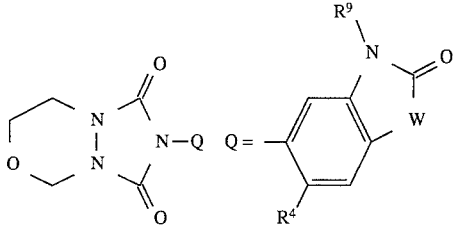

| R⁴ | R⁹ | w | melting point °C. |
|---|---|---|---|
| F | H | S | |
| F | CH₃ | S | |
| F | CH₂CH₃ | S | |
| F | CH₂C≡CH | S | |
| Cl | CH₂C≡CH | S | |
| F | CH(CH₃)C≡CH | S | |
| F | CH₂C≡CH | O | |
| Cl | H | S | |
| Cl | CH₃ | S | |
| Cl | CH₂CH₃ | S | |
| Cl | CH₂CH=CH₂ | S | |
| F | CH₂OCH₂ | S | |
| F | CH₂CH₂CH₃ | S | |
| Cl | CH(CH₃)C≡CH | S | |
| F | CH(CH₃)₂ | S | |
| F | CH₂CH=CH₂ | S | |
| Cl | CH₂CH=CH₂ | S | |
| F | CF₂CHF₂ | S | |
| Cl | CH₂C≡CH | O | |
| Cl | CH(CH₃)₂ | S | |
| Cl | CH₂CH₂CH₃ | S | |
| Cl | CF₂CHF₂ | S | |
| F | CH₂CH=CHCH₃ | S | |

TABLE 5

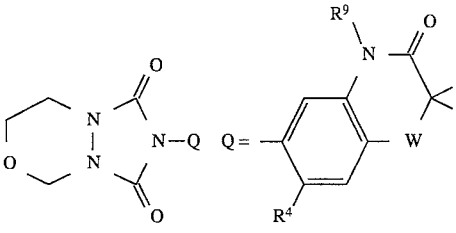

| R⁴ | R⁷ | R⁸ | R⁹ | w | melting point °C. |
|---|---|---|---|---|---|
| H | H | H | H | O | |
| F | H | H | CH₃ | O | |
| F | H | H | CH₂C≡CH | O | |
| F | H | H | CH(CH₃)C≡CH | O | |
| Cl | H | H | CH₂C≡CH | O | |
| F | CH₃ | H | CH₂C≡CH | O | |
| F | H | H | CH₂C≡CH | S | |
| Cl | H | H | CH₃ | O | |
| F | H | H | CH₂CH₃ | O | |
| F | H | H | CH₂CH₂CH₃ | O | |
| F | H | H | CH(CH₃)₂ | O | |
| F | H | H | CH₂C=CH₂ | O | |

TABLE 5-continued

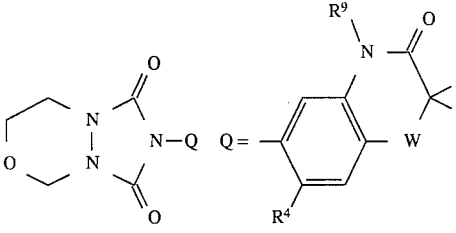

| R⁴ | R⁷ | R⁸ | R⁹ | w | melting point °C. |
|---|---|---|---|---|---|
| Cl | H | H | CH(CH₃)C≡CH | O | |
| Cl | H | H | CH₂C≡CH | S | |
| F | CH₃ | CH₃ | CH₂C≡CH | O | |
| F | H | H | H | O | |
| Cl | H | H | CH₂CH₃ | O | |
| Cl | H | H | CH(CH₃)₂ | O | |
| Cl | CH₃ | H | CH₂CH=CH₂ | O | |
| F | CH₃ | H | CH₂CH≡CH | O | |
| Cl | CH₃ | CH₃ | CH₂C≡CH | O | |
| Cl | CH₃ | CH₃ | CH₂CH=CH₂ | O | |
| Cl | H | H | CH₂CH₂CH₃ | O | |
| Cl | CH₃ | H | CH₂C≡CH | O | |

TABLE 6

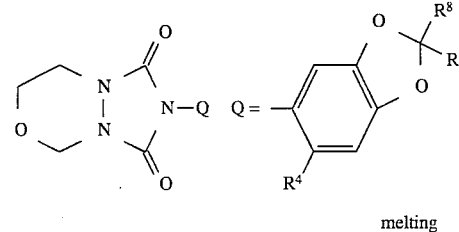

| R⁴ | R⁷ | R⁸ | melting point °C. |
|---|---|---|---|
| H | F | F | |
| F | F | F | |
| F | H | H | |

TABLE 7

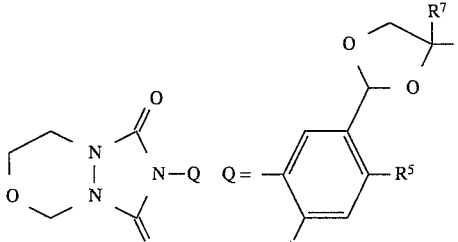

| R⁴ | R⁵ | R⁶ | R⁷ | melting point °C. |
|---|---|---|---|---|
| H | H | CO₂CH₃ | H | |
| H | H | CO₂CH₃ | CH₃ | |
| H | H | CO₂C₂H₅ | CH₃ | |
| H | H | CO₂C₂H₅ | H | |
| H | H | CO₂(CH₂)₂CH₃ | CH₃ | |
| H | H | CO₂(CH₂)₂CH₃ | H | |

TABLE 7-continued

Structure: morpholine-N-N(C=O)(C=O)-N-Q where Q = phenyl with R4, R5, and R6 = OCH2-CH(R7)(R6)-O (dioxolane type with R6, R7)

| R⁴ | R⁵ | R⁶ | R⁷ | melting point °C. |
|----|----|----|----|---|
| H | H | CO₂CH₂C≡CH | CH₃ | |
| H | Cl | CO₂CH₃ | CH₃ | |
| H | Cl | CO₂C₂H₅ | CH₃ | |
| H | Cl | CO₂(CH₂)₂CH₃ | CH₃ | |
| H | Cl | CO₂(CH₂)₃CH₃ | CH₃ | |
| H | Cl | CO₂CH₂C≡CH | CH₃ | |
| F | Cl | CO₂CH₃ | CH₃ | |
| F | Cl | CO₂C₂H₅ | CH₃ | |
| F | Cl | CO₂(CH₂)₂CH₃ | CH₃ | |
| F | Cl | CO₂(CH₂)₂CH₃ | H | |
| F | Cl | CO₂CH₂C≡CH | CH₃ | |
| F | Cl | CO₂CH(CH₃)C≡CH | CH₃ | |
| F | Cl | CO₂CHCH=CH₂ | CH₃ | |
| F | Cl | CO₂CH(CH₃)₂ | CH₃ | |
| F | Cl | CO₂(CH₂)₃CH₃ | CH₃ | |
| F | Cl | CO₂CH(CH₃)CH₂CH₃ | CH₃ | |
| Cl | Cl | CO₂(CH₂)₂CH₃ | CH₃ | |
| Cl | Cl | CO₂(CH₂)₃CH₃ | CH₃ | |
| Cl | Cl | CO₂CH(CH₃)₂ | CH₃ | |
| Cl | Cl | CO₂CH₃ | CH₃ | |
| Cl | Cl | CO₂CH₂CH₃ | CH₃ | |
| F | CN | CO₂(CH₂)₃CH₃ | CH₃ | |
| Cl | Cl | CO₂(CH₂)₂CH₃ | H | |
| F | CN | CO₂CH₃ | CH₃ | |
| F | CN | CO₂CH₂CH₃ | CH₃ | |
| Cl | CN | CO₂(CH₂)₃CH₃ | CH₃ | |
| Cl | Cl | CO₂CH₂C≡CH | CH₃ | |
| Cl | CN | CO₂CH₂C≡CH | CH₃ | |
| Cl | CN | CO₂CH(CH₃)C≡CH | CH₃ | |
| Cl | Cl | CO₂CH₂CH=CH₂ | CH₃ | |
| Cl | Cl | CO₂CH(CH₃)C≡CH | CH₃ | |

TABLE 8

Structure: morpholine-N-N(C=S)(C=O)-N-Q, Q = phenyl with R4, R5, R6

| R⁴ | R⁵ | R⁶ | melting point °C. |
|----|----|----|---|
| H | Cl | H | |
| Cl | Cl | H | 164–166 |
| F | Cl | OCH(CH₃)₂ | |
| F | Cl | OCH₂C≡CH | |
| F | Cl | OCH(CH₃)C≡CH | |
| F | Cl | OCH₂CH=CH₂ | |
| F | Cl | CO₂CH(CH₃)₂ | |

TABLE 8-continued

| R⁴ | R⁵ | R⁶ | melting point °C. |
|----|----|----|---|
| F | Cl | CO₂CH₂CH₂CH₃ | |
| F | Cl | CO₂CH₃ | |
| F | Cl | NHSO₂CH₃ | |
| F | Cl | NHSO₂CH(CH₃)₂ | |
| F | Cl | SCH(CH₃)₂ | |
| F | Cl | SCH₂CO₂CH₃ | |
| F | Cl | SCH₂CO₂H | |
| F | Cl | SCH₂C≡CH | |
| F | Cl | OCH₃ | |
| F | Cl | OCHF₂ | |

TABLE 9

Structure: morpholine-N-N(C=S)(C=O)-N-Q, Q = phenyl with R4 and substituent N(R9)-C(=w)-C(R7)(R8)-O-

| R⁴ | R⁷ | R⁸ | R⁹ | w | melting point °C. |
|----|----|----|----|---|---|
| F | H | H | CH₃ | O | |
| F | H | H | CH₂C≡CH | O | oil |
| F | H | H | CH₂CN | O | |
| F | H | H | CH₂CH=CH₂ | O | subl. 85° C. |
| F | H | H | CH(CH₃)CH₂CO₂CH₃ | O | |
| F | H | H | CH(CH₃)CH₂CO₂C₂H₅ | O | oil |
| F | H | H | CH(CH₃)C≡CH | O | |
| Cl | H | H | CH₂C≡CH | O | |
| Cl | H | H | CH₂CH=CH₂ | O | |
| F | H | H | CH₂C≡CH | S | |
| Cl | H | H | C₂H₅ | O | |
| F | H | H | C₂H₅ | O | |

TABLE 10

Structure: morpholine-N-N(C=O)(C=S)-N-Q, Q = phenyl with R4, R5, R6

| R⁴ | R⁵ | R⁶ | melting point °C. |
|----|----|----|---|
| H | Cl | H | |
| Cl | Cl | H | |
| F | Cl | OCH(CH₃)₂ | |
| F | Cl | OCH₂C≡CH | |

TABLE 10-continued

[Structure: morpholine ring with N connected to two C=O / C=S groups around N-Q, where Q = phenyl ring with R⁶ (ortho), R⁵ (para), R⁴ (meta)]

| $R^4$ | $R^5$ | $R^6$ | melting point °C. |
|---|---|---|---|
| F | Cl | $OCH(CH_3)C \equiv CH$ | |
| F | Cl | $OCH_2CH = CH_2$ | |
| F | Cl | $CO_2CH(CH_3)_2$ | |
| F | Cl | $CO_2CH_2CH_2CH_3$ | |
| F | Cl | $CO_2CH_3$ | |
| F | Cl | $NHSO_2CH_3$ | |
| F | Cl | $NHSO_2CH(CH_3)_2$ | |
| F | Cl | $SCH(CH_3)_2$ | |
| F | Cl | $SCH_2CO_2CH_3$ | |
| F | Cl | $SCH_2CO_2H$ | |
| F | Cl | $SCH_2C \equiv CH$ | |
| F | Cl | $OCH_3$ | |
| F | Cl | $OCHF_2$ | |

Formulations

Useful formulations of the compounds of Formula 1 can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to about 99% by weight of active ingredient(s) and at least one of (a) up to about 20% surfactant(s) and (b) up to about 99.9% solid or liquid diluent(s). Note specifically, they will contain these ingredients in the following approximate proportions:

| | Weight Percent | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

Active ingredient plus at least one of a surfactant or a diluent equals 100 weight percent. Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dotland Books, Caldwell. N.J., but other solids, either mined or manufactured, may be used. The more absorptive diluents are preferred for wettable powders and the denser ones for dusts. Typical liquid diluents and solvents are described in Marsden, "Solvents Guide", 2nd Ed.. Interscience, New York. 1950. Solubility under 0.1% is preferred for suspension concentrates; solutions concentrates are preferably stable against phase separation at 0° C. "McCutcheon's Detergents and Emulsifiers Annual". MC Publishing Corp.. Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

Granules and pellets may be made by spraying the active material upon preformed granular carriers or by agglomeration techniques. See J. E. Browning, "Agglomeration", *Chemical Engineering,* Dec. 4, 1967, pp. 147ff and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, March 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook". 5th Ed., Blackwell Scientific Publications, Oxford, 1968, pp. 101–103.

In the following examples, all parts are by weight unless otherwise indicated.

Example A

Wettable Powder

| | |
|---|---|
| 8-(4'-chloro-2'-fluoro-5'-carboisopropoxyphenyl)-4-oxa-7,9-dioxo-1,2,8-triazabicyclo-[4.3.0]nonane | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns. reblended and packaged.

Example B

Wettable Powder

| | |
|---|---|
| 8-(4'-chloro-2'-fluoro-5'-carboisopropoxyphenyl)-4-oxa-7,9-dioxo-1,2,8-triazabicyclo-[4.3.0]nonane | 50% |
| sodium alkylnaphthalenesulfonate | 2% |

| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

Example C

Granule

| Wettable Powder of Example B | 5% |
| attapulgite granules (U.S.S. 20–40 mesh; 0,84–0,42 mm) | 95% |

A slurry of wettable powder containing 25% solids is sprayed on the surface of attapulgite granules in a double-cone blender. The granules are dried and packaged.

Example D

Extruded Pellet

| 8-(4'-chloro-2'-fluoro-5'-carboisopropoxyphenyl)-4-oxa-7,9-dioxo-1,2,8-triazabicyclo-[4.3.0]nonane | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

Example E

Low Strength Granule

| 8-(4'-chloro-2'-fluoro-5'-carboisopropoxyphenyl)-4-oxa-7,9-dioxo-1,2,8-triazabicyclo-[4.3.0]nonane | 1% |
| N,N-dimethylformamide | 9% |
| attapulgite granules (U.S.S. 20 to 40 sieve) | 90% |

The active ingredient is dissolved in the solvent and the solution is sprayed upon dedusted granules in a double-cone blender. After spraying of the solution has been completed, the blender is allowed to run for a short period and then the granules are packaged.

Example F

Granule

| 8-(4'-chloro-2'-fluoro-5'-carboisopropoxyphenyl)-4-oxa-7,9-dioxo-1,2,8-triazabicyclo-[4.3.0]nonane | 80% |
| wetting agent | 1% |
| crude lingninsulfonate salt (containing 5–20% of the natural sugars) | 10% |
| attapulgite clay | 9% |

The ingredients are blended and milled to pass through a 0.15 mm (100 mesh) screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionall with heat until the water content is reduced to the desired level, generally, less than 1%. The material is then discharged, screened to the desired size range, generally 1.4 mm–0.15 mm (14–100 mesh). and packaged for use.

Example G

Aqueous Suspension

| 8-(4'-chloro-2'-fluoro-5'-carboisopropoxyphenyl)-4-oxa-7,9-dioxo-1,2,8-triazabicyclo-[4.3.0]nonane | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

Example H

High Strength Concentrate

| 8-(4'-chloro-2'-fluoro-5'-carboisopropoxyphenyl)-4-oxa-7,9-dioxo-1,2,8-triazabicyclo-[4.3.0]nonane | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

Example I

Wettable Powder

| 8-(4'-chloro-2'-fluoro-5'-carboisopropoxyphenyl)-4-oxa-7,9-dioxo-1,2,8-triazabicyclo-[4.3.0]nonane | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen (0.3 mm) and then packaged.

Example J

Wettable Powder

| | |
|---|---|
| 8-(4'-chloro-2'-fluoro-5'-carboisopropoxyphenyl)-4-oxa-7,9-dioxo-1,2,8-triazabicyclo[4.3.0]nonane | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

Example K

Oil Suspension

| | |
|---|---|
| 8-(4'-chloro-2'-fluoro-5'-carboisopropoxyphenyl)-4-oxa-7,9-dioxo-1,2,8-triazabicyclo[4.3.0]nonane | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Example L

Dust

| | |
|---|---|
| 8-(4'-chloro-2'-fluoro-5'-carboisopropoxyphenyl)-4-oxa-7,9-dioxo-1,2,8-triazabicyclo[4.3.0]nonane | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

Example M

Oil Suspension

| | |
|---|---|
| 8-(4'-chloro-2'-fluoro-5'-carboisopropoxyphenyl)-4-oxa-7,9-dioxo-1,2,8-triazabicyclo[4.3.0]nonane | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Utility

The compounds of the present invention are active herbicides. They have utility for broadspectrum preemergence and/or postemergence weed control in areas where complete control of all vegetation is desired, such as around industrial complexes, storage areas, parking lots, drive-in theaters, around billboards, fence rows, highway and railroad structures. Some of the compounds have utility for selective weed control in crops such as rice, wheat, barley, corn, soybeans, sugarbeets, cotton, peanut, all plantation crops including coffee, cocoa, sugarcane, oil palm, rubber, citrus, grapes, fruit trees, nut trees, banana, plantain, pineapple and conifers such as loblolly pine.

The compounds can be applied as a preemergence and/or postemergence treatment using techniques of banding, directed sprays or broadcast applications. The rates of application for the compounds of the invention are determined by a number of factors, including their use as selective or general herbicides, the crop species involved, the types of weeds to be controlled, weather, climate, formulations selected, mode of application, amount of foliage present, etc. By selecting the appropriate rate which would be apparent to one skilled in the art, the compounds of this invention can be used in areas where complete control of all vegetation is desired, such as around fuel storage tanks, ammunition depots, industrial storage areas, oil well sites, drive-in theaters, around billboards, highway and railroad structures and in fence rows. Alternatively, by selecting the proper rates and adjuvants, the compounds of this invention can be used for selective weeds control in peanuts and plantation corps such as citrus, sugarecane, coffee, oil palm, rubber, cocoa, grapes, fruit trees, nut trees, pineapple and banana. In general, the subject compounds are applied at levels of around 0.001 to 20 kg/ha, with a preferred rate range of 0.01 to 2 kg/ha rate. One skilled in the art can select the proper rates for a given situation.

The compounds of this invention may be used in combination with other herbicides listed below. They are particularly useful in combination with triazine, triazole, uracil, urea, amide, carbamate, bipyridylium, phenoxy, sulfonylurea and imidazole types for total vegetation control in plantation and other crops. The compounds may also be used in combination with mefluidide, glyphosate or gluphosinate.

A mixture of one or more of the following herbicides with a compound of this invention may be particularly useful for weed control. Examples of other herbicides with which compounds of this invention can be formulated are:

acetochlor, acifluorfen, acrolein, 2-propenal, alachlor, ametryn, amidosulfuron, ammonium sulfamate, amitrole, anilofos, asulam, atrazine, barban, benefin, bensulfuron methyl, bensulide, bentazon, benzofluor, benzoylprop, bifenox, bromacil, bromoxynil, bomoxynil heptanoate, bromoxynil octanoate, butachlor, buthidazole, butralin, butylate, cacodylic acid, 2-chloro-N,N-di-2-propenylacetamide, 2-chloroallyl diethyldithiocarbamate, chloramben, chlorbromuron, chloridazon, chlorimuron ethyl, chlormethoxynil, chlornitrofen, chloroxuron, chlorpropham, chlorsulfuron, chlortoluron, cinmethylin, cinosulfuron, clethodium, clomazone, cloproxydim, clopyralid, calcium salt-or methylarsonic acid, cyanazine, cycloate, cyluron, cyperquat, cyprazine, cyprazole, cypromid, dalapon, dazomet, dimethyl 2,3,5,6-tetrachloro-1,4-benzenedicarboxylate, desmedipham, desmetryn, dicamba, dichlobenil, dichlorprop, diclofop, diethatyl, difenzoquat, diflufenican, dimepiperate, dinitramine, dinoseb, diphenamid, dipropetryn, diquat, diuron, 2-methyl-4,6-dinitrophenol, disodium salt of methylarsonic acid, dymron, endothall, S-ethyl dipropylcarbamothioate, esprocarb, ethalfluralin, ethametsulfuron methyl, ethofumesate, fenac, fenoxaprop, fenuron, salt of fenuron and trichloroacetic acid, flamprop, fluazifop, fluazifop-P, fluchloralin, flumesulam, flumipropyn, fluometuron, fluorochloridone, fluorodifen, fluoroglycofen, flupoxam, fluridone, fluoroxypyr, fluzasulfuron, fomesafen, fosamine, glyphosate, haloxyfop, hexaflurate, hexazinone, imazamethabenz, imazapyr, imazaquin, imazamethabenz methyl, imazethapyr, imazosulfuron, ioxynil, isopropalin, isoproturon, isouron, isoxaben, karbutilate, lactofen, lenacil, linuron, metobenzuron, metsulfuron methyl, methylarsonic acid, monoammonium salt of methylarsonic acid, (4-chloro-2-methylphenoxy)acetic acid, S,S'-dimethyl-2-(difluoromethyl)-4-(2-methylpropyl)-6-(trifluoromethyl)-3,5-pyridinedicarbothioate. mecoprop, mefenacet, mefluidide, methalpropalin, methabenzthiazuron, metham, methazole, methoxuron, metolachlorol metribuzin, 1,2-dihydropytidazine-3,6-dione, molinate, monolinuron, monuron, monuron salt and trichloroacetic acid, monosodium salt of methylarsonic acid, napropamide, naptalam, neburon, nicosulfuron, nitralin, nitrogen, nitrofluorfen, norea, norflurazon, oryzalin, oxadiazon, oxyfluorfen, paraquat, pebulate, pendimethalin, perfluidone, phenmedipham, picloram, 5-[2-chloro-4(trifluormethyl)phenoxy]-2-nitroacetophenone oxime-O-acetic acid methyl ester, pretilachlor, primisulfuron, procyazine, profluralin, prometon, prometryn, pronamide, propachlor, propanil, propazine, propham, prosulfalin, prynachlor, pyrazolate, pyrazon, pyrazosulfuron ethyl, quinchlotac, quizalofop ethyl, rimsulfuron secbumeton, sethoxydim, siduron, simazine, 1-(a,a-dimethylbenzyl)-3-(4-methylphenyl)urea, sulfometuron methyl, trichloroacetic acid, tebuthiuron, terbacil, terbuchlor, terbuthylazine, terbutol, terbutryn, thifensulfuron methyl, thiobencarb, tri-allate, trialkoxydim, triasulfuron, tribenuron methyl, triclopyr, tridiphane, trifluralin, trimeturon, (2,4-dichlorophenoxy)acetic acid, 4-(2,4-dichlorophenoxy)butanoic acid, vernolate, and xylachlor.

The herbicidal properties of the subject compounds were discovered in a number of greenhouse tests. The test procedures and results are as follows:

Biological tables

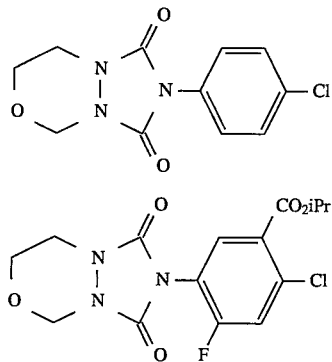

compound 1 compound 2

-continued
Biological tables

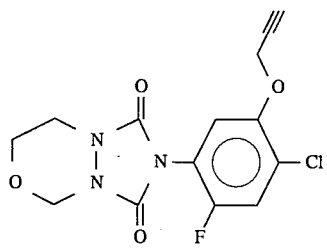

compound 3

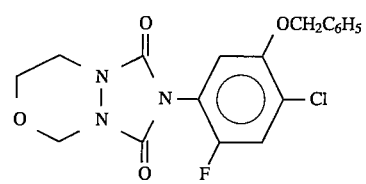

compound 4

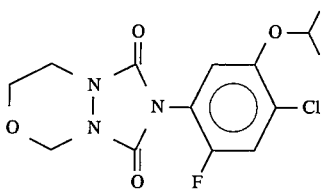

compound 5

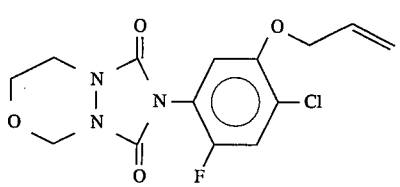

compound 6

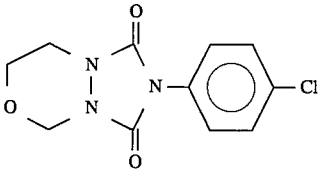

compound 7

Test procedure

Seeds of crabgrass (*Digitaria spp.*), barnyardgrass (*Echinochloa crus-galli*), giant foxtail (*Setaria faberii*), wild oats (*Avena fatua*), cheatgrass (*Bromus secalinus*), velvetleaf (*Abutilon theophrasti*), morningglory (*Ipomoea spp.*), cocklebur (*Xanthium pensylvanicum*) and sorghum. Nutsedge tubers were planted and treated preemergence with the test chemicals dissolved in a non-phytotoxic solvent. At the same time, these weed species were treated with a soil/foliage application. At the time of treatment, the plants ranged in height from 2 to 18 cm. Treated plants and controls were maintained in a greenhouse for sixteen days, after which all species were visually rated for response to treatment and compared to controls. The ratings, summarized in Table A, are based on a numerical scale extending from 0=no injury, to 10=complete kill.

The accompanying descriptive symbols have the following meanings:
C=chlorosis/necrosis;
B=burn
H=formative effect;
G=growth retardation;
E=emergence inhibition.

TABLE A

| | \multicolumn{7}{c}{postemergence (application rate 2 kg a.i./ha)} | | | | | | |
|---|---|---|---|---|---|---|---|
| | Comp. 1 | Comp. 2 | Comp. 3 | Comp. 4 | Comp. 5 | Comp. 6 | Comp. 7 |
| Barnyardgrass | 10B | 10 | 10 | 10 | 10 | 10 | 10 |
| Cocklebur | 10B | 10 | 10 | 10 | 10 | 10 | 10 |
| Morningglory | 10B | 10 | 10 | 10 | 10 | 10 | 10 |
| Sorghum | 10B | 10 | 10 | 10 | 10 | 10 | 10 |
| Giant foxtail | 10B | 10 | 10 | 10 | 10 | 10 | 10 |
| Crabgrass | 10B | 10 | 10 | 10 | 10 | 10 | 10 |
| Velvetleaf | 10B | 10 | 10 | 10 | 10 | 10 | 10 |

TABLE B

| | preemergence (application rate 2 kg a.i./ha) | | | | | | |
|---|---|---|---|---|---|---|---|
| | Comp. 1 | Comp. 2 | Comp. 3 | Comp. 4 | Comp. 5 | Comp. 6 | Comp. 7 |
| Barnyardgrass | 9B | 10 | 10 | 10 | 10 | 10 | 10 |
| Cocklebur | 10B | 10 | 10 | 10 | 10 | 10 | 10 |
| Morningglory | 10B | 10 | 10 | 10 | 10 | 10 | 10 |
| Sorghum | 10B | 10 | 10 | 10 | 10 | 10 | 10 |
| Giant foxtail | 10B | 10 | 10 | 10 | 10 | 10 | 10 |
| Crabgrass | 9B | 10 | 10 | 10 | 10 | 10 | 10 |
| Velvetleaf | 10B | 10 | 10 | 10 | 10 | 10 | 10 |

TABLE C

| | postemergene (application rate 0.2 kg a.i./ha) | | | | | | |
|---|---|---|---|---|---|---|---|
| | Comp. 1 | Comp. 2 | Comp. 3 | Comp. 4 | Comp. 5 | Comp. 6 | Comp. 7 |
| Corn | 2B | 9 | 9 | 3 | 9 | 10 | 2B |
| Wheat | 0 | 10 | 4 | 4 | 9 | 9 | 5B |
| Barnyardgrass | 2B | 10 | 10 | 10 | 10 | 10 | 6B |
| Cocklebur | 2B | 10 | 10 | 9 | 9 | 10 | 7B |
| Morningglory | 7B | 10 | 10 | 9 | 10 | 10 | 9B |
| Sorghum | 3B | 10 | 10 | 9 | 10 | 10 | 4B |
| Giant foxtail | 4B | 10 | 10 | 10 | 10 | 10 | 4B |
| Crabgrass | 3B | 10 | 10 | 9 | 9 | 10 | 3B |
| Velvetleaf | 8B | 10 | 10 | 9 | 10 | 10 | 9B |

TABLE D

| | preemergence (application rate 0.2 kg a.i./ha) | | | | | | |
|---|---|---|---|---|---|---|---|
| | Comp. 1 | Comp. 2 | Comp. 3 | Comp. 4 | Comp. 5 | Comp. 6 | Comp. 7 |
| Corn | 0 | 8 | 9 | 2 | 8 | 10 | 0 |
| Wheat | 0 | 8 | 9 | 4 | 6 | 9 | 2G |
| Barnyardgrass | 3G | 10 | 10 | 9 | 10 | 10 | 6H |
| Cocklebur | 0 | 10 | 10 | 9 | 9 | 9 | 3G |
| Morningglory | 1C | 10 | 10 | 9 | 10 | 10 | 3H |
| Sorghum | 0 | 10 | 10 | 8 | 9 | 10 | 1C |
| Giant foxtail | 0 | 10 | 10 | 9 | 9 | 10 | 7H |
| Crabgrass | 0 | 9 | 10 | 9 | 9 | 9 | 8G |
| Velvetleaf | 7H | 10 | 10 | 9 | 10 | 10 | 10C |

What is claimed is:

1. Anellated triazole compounds formula I

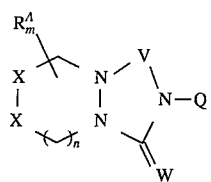

wherein

X—X is C—O;

m is 0 to 6;

n is 1;

V is —C(=W)—;

W is O or S;

$R^A$ is independently selected from the group: hydrogen; hydroxy; $CO_2H$; $CO_2R^2$; halogen; CN; $C(O)NR^{11}R^{12}$; $OR^3$: $(C_1-C_8)$alkyl; $(C_2-C_8)$haloalkyl; $(C_2-C_8)$alkenyl; $(C_2-C_8)$alkynyl; $S(O)_nR_3$; $C(O)R^3$; or $C(O)SR^2$; or two $R^A$ groups attached to the same carbon are taken together along with the carbon atom to which they are attached to form C=O;

Q is

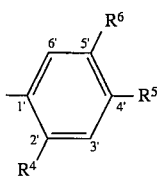 Q-1

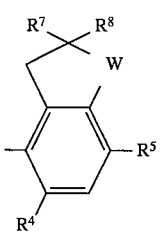 Q-2

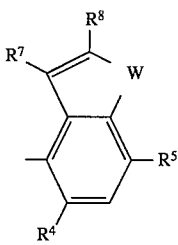 Q-3

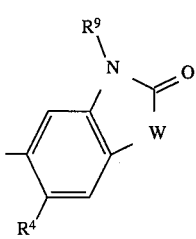 Q-4

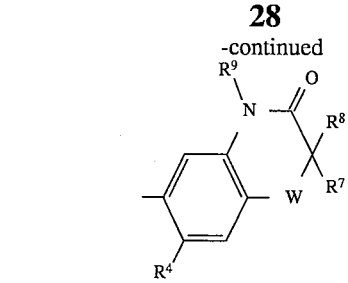 Q-5

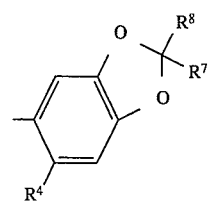 Q-6

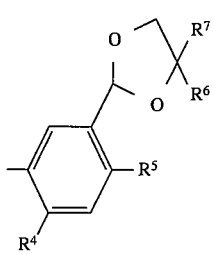 Q-7

$R^1$ is hydrogen, hydroxy, halogen, CN, $(C_1-C_8)$alkyl, $(C_1-C_8)$haloalkyl, $(C_1-C_8)$alkenyl, $(C_1-C_8)$alkynyl, $COR^3$, CHO, $OR^3$, $C(O)SR^2$, $CO_2R^2$ or $C(O)NR^{11}R^{12}$;

$R^2$ is hydrogen, $(C_1-C_8)$alkyl, $(C_1-C_8)$haloalkyl, $(C_1-C_8)$alkenyl, $(C_1-C_8)$alkynyl, or $COR^3$;

$R^3$ is $(C_1-C_8)$alkyl, $(C_3-C_8)$cycloalkyl, $(C_3-C_8)$alkenyl, $(C_3-C_8)$alkynyl, $(C_1-C_8)$haloalkyl, $(C_2-C_8)$alkoxyalkyl, $(C_2-C_4)$carboxy alkyl, $(C_3-C_8)$alkoxycarbonylalkyl, $(C_4-C_8)$alkenyloxyalkyl, $(C_4-C_8)$alkynyloxyalkyl, $(C_4-C_8)$haloalkoxyalkyl, $(C_4-C_8)$trialkylsilyl, $(C_3-C_8)$cyanoalkyl, $(C_3-C_8)$haloalkenyl, $(C_3-C_8)$haloalkynyl, $(C_2-C_8)$alkylcarbonyl, $(C_2-C_8)$alkoxycarbonyl, $(C_2-C_8)$haloalkoxycarbonyl, $p(O)(OR^{17})_2$, $CHR^{16}P(O)(OR^{17})_2$ or $CHR^{16}P(S)(OR^{17})_2$, phenyl or benzyl, said phenyl or benzyl being optionally substituted with halogen, $(C_1-C_3)$alkyl, $(C_1-C_3)$haloalkyl or $(C_1-C_4)$alkoxy:

$R^4$ is hydrogen or halogen;

$R^5$ is $(C_1-C_2)$alkyl, $(C_1-C_2)$haloalkyl, $OCH_3$, $SCH_3$, $OCHF_2$, halogen, CN or $NH_2$;

$R^6$ is hydrogen, $(C_1-C_8)$alkyl, $(C_1-C_8)$haloalkyl, $CO_2R^{10}$ halogen, $OR^{10}$, $S(O)_nR^{10}$, $COR^{10}$, $C(O)SR^{10}$, $CO_2R^{10}$, $SCH_2C\equiv CH$, $C(O)NR^{11}R^{12}$, CHO, $CH=CHCO_2R^{10}$, $CO_2N=CR^{13}R^{14}$, $NO_2$, CN, $NHSO_2R^{15}$ or $NHSO_2NHR^{15}$;

$R^7$ and $R^8$ are independently hydrogen, $(C_1-C_3)$alkyl, $(C_1-C_3)$haloalkyl or halogen, or when Q is Q-2, Q-5 or Q-6, then $R^7$ and $R^8$ together with the carbon to which they are attached are additionally selected from C=O;

$R^9$ is hydrogen, $(Cl_1-C_6)$alkyl, $(C_1-C_6)$haloalkyl, $(C_2-C_6)$alkoxyalkyl, $(C_3-C_6)$alkenyl or $(C_3-C_6)$alkynyl;

$R^{10}$ is $(C_1-C_8)$alkyl, $(C_3-C_8)$cycloalkyl, $(C_3-C_8)$alkenyl, $(C_3-C_8)$alkynyl, $(C_1-C_8)$haloalkyl, $(C_2-C_8)$alkoxyalkyl, $(C_2-C_6)$alkylthioalkyl, $(C_2-C_8)$alkylsulfinylalkyl, $(C_2-C_8)$alkylsulfonylalkyl, $(C_3-C_8)$alkoxyalkoxyalkyl, $(C_4-C_8)$cycloalkylalkyl, $(C_2-C_4)$carboxyalkyl, $(C_3-C_8)$alkoxycarbonylalkyl, $(C_6-C_8)$alkenyloxycarbonylalkyl, $(C_6-C_8)$alkynyloxycarbonylalkyl, $(C_6-C_8)$cycloalkoxyalkyl, $(C_4-C_8)$alkenyloxyalkyl, $(C_4-C_8)$alkynyloxyalkyl $(C_3-C_8)$haloalkoxyalkyl, $(C_4-C_8)$haloalkenyloxyalkyl, $(C_4-C_8)$haloalkynyloxyalkyl, $(C_6-C_8)$cycloalkylthioalkyl, $(C_4-C_8)$alkenylthioalkyl, $(C_4-C_8)$alkynylthioalkyl, $(C_4-C_8)$trialkylsilylalkyl, $(C_3-C_8)$cyanoalkyl, $(C_3-C_8)$halocycloalkyl, $(C_3-C_8)$haloalkenyl, $(C_5-C_8)$alkoxyalkenyl, $(C_5-C_8)$haloalkoxyalkenyl, $(C_5-C_8)$alkylthioalkenyl, $(C_3-C_8)$haloalkynyl, $(C_5-C_8)$alkoxyalkynyl, $(C_5-C_8)$haloalkoxyalkynyl, $(C_5-C_8)$alkylthioalkynyl, $(C_2-C_8)$alkylcarbonyl, $CHR^{16}COR^{17}$, $CHR^{16}P(O)(OR^{17})_2$, $P(O)(OR^{17})_2$, $CHR^{16}P(S)(OR^{17})_2$, $CHR^{16}C(O)HR^{11}R^{12}$, $CHR^{16}C(O)NH_2$, $(C_1-C_4)$alkyl substituted with phenoxy or benzyloxy, said phenoxy or benzyloxy being optionally substituted with halogen, $(C_1-C_3)$alkyl or $(C_1-C_3)$haloalkyl; benzyl optionally substituted with halogen, $(C_1-C_8)$alkyl or $(C_1-C_3)$haloalkyl; or phenyl or pyridyl each optionally substituted with halogen, $(C_1-C_3)$alkyl, $(C_1-C_3)$haloalkyl or $(C_1-C_4)$alkoxy;

$R^{11}$ and $R^{13}$ are independently hydrogen or $(C_1-C_4)$alkyl;

$R^{12}$ and $R^{14}$ are independently $(C_1-C_4)$alkyl, phenyl optionally substituted with halogen, $(C_1-C_3)$alkyl, $(C_1-C_3)$haloalkyl or $(C_1-C_4)$alkoxy; or $R^{11}$ and $R^{12}$ are taken together as $-(CH_2)_5-$, $-(CH_2)_4-$ or $-CH_2CH_2OCH_2CH_2-$, each ring optionally substituted with $(C_1-C_3)$alkyl, phenyl or benzyl; or $R^{13}$ and $R^{14}$ are taken together with the carbon to which they are attached to form $(C_3-C_8)$cycloalkyl;

$R^{15}$ is $(C_1-C_4)$alkyl or $(C_1-C_4)$haloalkyl;

$R^{16}$ is hydrogen or $(C_1-C_3)$alkyl;

$R^{17}$ is $(C_1-C_6)$alkyl, $(C_3-C_6)$alkenyl or $(C_3-C_6)$alkynyl;

$R^{18}$ is hydrogen, hydroxy, CN, $(C_1-C_8)$alkyl, $(C_1-C_8$haloalkyl, $(C_1-C_8$alkenyl, $(C_1-C_8)$alkynyl, $COR^3$, CHO, $OR^3$, $C(O)SR^2$, $CO_2R^2$ or $C(O)NR^{11}R^{12}$.

2. Anellated triazole compounds according to claim 1, wherein the organic residue of $R^A$ is hydrogen, hydroxy, $OR^3$, halogen, $(C_1-C_8)$alkyl, $(C_1-C_8)$haloalkyl, $(C_2-C_8)$alkenyl, $(C_2-C_8)$alkynyl, $S(O)_nR^3$, $COR^3$, $CO_2R^2$, $C(O)SR^2$, $C(O)NR^{11}R^{12}$ or CN.

3. Anellated triazole compounds according to claim 2, wherein $R^A$ is hydrogen.

4. Anellated triazole compounds according to claim 2, wherein X—X is C—O.

5. Anellated triazole compounds according to claim 2, wherein V is

and W is O.

6. Anellated triazole compounds according to claim 2, wherein Q is Q-1.

7. Method for preparing anellated triazoles according to claim 1 comprising:

reacting a compound of formula III

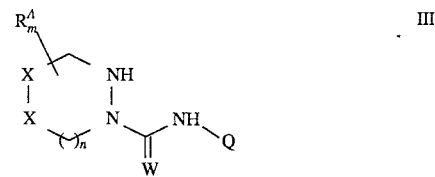

with phosgene or a phosgene substitute optionally in the presence of a solvent and optionally in the presence of an acid acceptor.

8. A composition suitable for controlling the growth of undesired vegetation which comprises an effective amount of a compound of claim 1 and at least one of the following: surfactant, solid or liquid diluent.

9. Method for combating undesired plants comprising applying an herbicidally effective amount of a compound of claim 1 to the undesired plants or to the soil.

10. Herbicidal agents characterized by a content of a compound of formula I of claim 1.

* * * * *